United States Patent [19]

Leusner et al.

[11] Patent Number: 4,981,875

[45] Date of Patent: Jan. 1, 1991

[54] MEDICAMENTS FOR THE REGION OF THE ORAL CAVITY

[75] Inventors: Bernd Leusner, Leverkusen; Rüdiger Heiss, Grefrath; Bernd Pelster, St. Augustin; Wolfgang Fischer, Bergisch Gladbach; Ulrich Ohm, Odenthal, all of Fed. Rep. of Germany

[73] Assignee: Bayer Aktiengesellschaft, Leverkusen, Fed. Rep. of Germany

[21] Appl. No.: 223,144

[22] Filed: Jul. 22, 1988

[30] Foreign Application Priority Data

Aug. 12, 1987 [DE] Fed. Rep. of Germany ....... 3726797

[51] Int. Cl.⁵ .................... A61K 9/107; A61K 31/195
[52] U.S. Cl. ....................................... 514/774; 424/80;
424/81; 424/435; 424/49; 560/47; 514/536;
514/944; 514/950; 514/900; 514/901; 514/902;
514/969; 514/777; 514/779; 514/781; 514/782;
514/784
[58] Field of Search .................. 560/47; 514/900, 901,
514/902, 969, 536, 944, 950, 777, 774, 779, 781,
782, 784; 424/49

[56] References Cited

U.S. PATENT DOCUMENTS

| | | |
|---|---|---|
| 4,623,346 | 11/1986 | von Bittera et al. ................. 424/449 |
| 4,627,852 | 12/1986 | von Bittera et al. ................. 514/375 |
| 4,746,675 | 5/1988 | Makino et al. ........................ 514/947 |
| 4,772,470 | 9/1988 | Inoue et al. ............................ 424/81 |
| 4,789,667 | 12/1988 | Makino et al. ........................ 514/946 |
| 4,871,767 | 10/1989 | Beckermann et al. ............... 514/936 |

FOREIGN PATENT DOCUMENTS 0130524 1/1985 European Pat. Off. .

OTHER PUBLICATIONS

The Merck Index, Tenth Edition, Published by Merck & Co., Inc., Rahway, N.J., 1983, p. 559, item 3824.
Chemical Abstracts, Band 76, Nr. 1, 3, Jan. 1972, Seite 31, Zusammenfassung Nr. 277q, Columbus, Ohio, U.S.; A. D. Inglot et al.
"Topical Treatment of Cutaneous Herpes Simplex in Humans with the Non—Steroid Antiinflammatory Drugs Mefenamic Acid and Indomethacim in Demethylsulfoxide", & Arch. Immunol. Ther. Exp., 1971 19 (4), 555–66, *Zusammenfassung, ins bensondere Formel I*.

*Primary Examiner*—Ronald W. Griffin
*Attorney, Agent, or Firm*—Sprung Horn Kramer & Woods

[57] ABSTRACT

Etofenamate is used for the preparation of compositions useful in the treatment of bacterial, viral or fungicidal inflammations in the region of the oral cavity.

9 Claims, No Drawings

MEDICAMENTS FOR THE REGION OF THE ORAL CAVITY

The invention relates to the use of etofenamate for the preparation of medicaments for the region of the oral cavity, to corresponding medicaments, and to the preparation thereof.

Etofenamate (INN) (2-(2-hydroxyethoxy)-ethyl-N-(α, α, α-trifluoro-m-tolyl)-anthranilate) is a known active compound with strong antiinflammatory activity (Arzneim. Forschung 27 (I), 6b (1977) 1326-1333). Etofenamate is used as active compound for the treatment of traumatically-related inflammations, for example following crush or impact injuries. This group of inflammations also includes rheumatically-related inflammations of joints and soft tissues.

Etofenamate-containing medicaments are, as a rule, in the form of a gel or cream which are applied to the dry skin. Gels contain as adjuvants for example polyacrylic acids, water and isopropanol (DAB 9, 1986 edition, page 1186); these gels and creams are not suitable for non-topical applications.

The use of etofenamate for the preparation of medicaments for the treatment of inflammations in the region of the oral cavity which are bacterial, viral or caused by fungi have been found.

It is surprising that etofenamate can also be employed for inflammations which are bacterial, viral or caused by fungi besides the use for traumatically-related inflammations.

This applies in particular to inflammations of the oral mucosa which are bacterial, viral or due to fungi. Medicaments for the region of the oral cavity must exhibit good adhesion to the tissue under the conditions of the environment of the mouth, high stability, a high liberation rate and high acceptance by the patient. No etofenamate preparations which comply with this purpose have hitherto been disclosed. The new medicaments which are prepared according to the invention in a manner known per se comply to a high degree with these requirements and thus are to be termed an advance in the technology.

Possible examples of inflammations in the region of the oral cavity due to bacteria or viruses are pulpitis, gingivitis, (apical) periodontitis, teething syndrome, stomatitis and aphthae. An example of a fungal infection of the oral mucosa which may be mentioned here is candidiasis (thrush). The medicaments according to the invention are preferably used for the treatment of gingivitis and periodontitis. The medicaments are also employed for the treatment of denture-related mucosal lesions and for the treatment of wounds following interventions in dental surgery, oral surgery and periodontal surgery.

In general, the medicaments according to the invention contain etofenamate in up to 20 per cent by weight, preferably 1 to 10 per cent by weight, based on the formulation. Particularly preferred are preparation$ having 2 to 8 per cent by weight of etofenamate.

It is, of course, also possible for the medicaments according to the invention to contain other active compounds or active auxiliaries besides etofenamate. Examples which may be mentioned are:

Local anaesthetics (for example tetracaine, benzocaine, procaine, lidocaine and salts thereof)
Chemotherapeutics (for example sulphanilamide)
Antibiotics (for example neomycin, tyrothricin, chlorotetracycline hydrochloride)
Antimycotics (for example clotrimazole, bifonazole, nystatin, miconazole, amphotericin B)
Disinfectants (for example benzalkonium chloride, dequalinium chloride, chinosolum chlorhexidine digluconate, thymol) Plant extracts (for example chamazulene, extr. flor. chamomillae)
Astringents (for example tannin, aluminum chloride)

The medicaments according to the invention can be in the form of semi-solid or liquid preparations. Liquid preparations can be formulated, for example, in the form of mouthwashes, tinctures or aerosols. Semi-solid medicaments can be ointments, creams, gels, emulsions or pastes. The medicaments can also be added to wound dressings such as are u$ed, for example, following interventions in periodontal surgery. It is equally possible to add the medicaments to denture adhesives (for example for immediate and interim dentures and in cases of denture stomatitis). Furthermore, the medicaments can be used in medicated inlays for pulpitis therapy (indirect or direct capping) and in endodontic treatments. In a particular embodiment of the present invention, etofenamate is in the form of an adhesive emulsion.

Components for the adhesive emulsion according to the invention are hydrophilic auxiliaries. These take the form of purely natural or semi-synthetic or completely synthetic polymers which, besides their swellability, achieve good adhesion on the oral mucosa.

Examples of natural polymers which may be mentioned are:

Gelatin: gelatin is a purified protein obtained by either partial acid (type A) or alkaline (type B) hydrolysis of animal collagen. The substance can also consist of a mixture of the two types.

Pectin: Pectins consist essentially of chains of galacturonic acid units with 1,4-o-glycosidic links, the acid groups thereof being 20 to 70% esterified with methanol. The pectins form elongate macromolecules which also contain a little galactose and arabinose in addition and have weakly acidic properties. Citrus pectins of molecular weight about 150,000 to 300,000 are preferred.

Alginic acid or sodium alginate: Polymannuronic acid obtained from brown algae, or the alkaline earth metal salts thereof, for example sodium or potassium salt and ammonium salt.

Gum arabic: Gum arabic is a gum-like secretion which hardens in air and emerges naturally, or after incision of the trunk and the branches, from Acacia senegal L. Willdenow or other African Acacia species.

Tragacanth: Tragacanth is a gum-like secretion which hardens in air and flows out naturally, or after incision, from the trunk and branches of Astragalus gummifer Labillardere and of certain other West Asiatic species of the genus Astragalus. Galactomannan: Galactomannan is a polymer of mannose and galactose.

Karaya gum: Karaya gum is a gum-like secretion which hardens in air and flows out naturally, or after incision, from the trunk and branches of
Sterculia species.

Examples of semi-synthetic polymers which may be mentioned are:

Cellulose ethers such as methyl-, methylhydroxyethyl-, hydroxymethyl-, ethyl-, propyl- or hydroxypropylmethylcellulose or carboxymethylcellulose and the sodium salts thereof.

Examples of synthetic polymers which may be mentioned are:
Polymethacrylic acid and the salts thereof
Polymethylmethacrylic acid and the salts thereof
Polyvinylpyrrolidone The stirring of the pasty composition is then continued for some hours until swelling is complete and, after cooling, flavorings are added where appropriate.

The resulting emulsion is stable in this composition without addition of emulsifiers.

Examples 1 to 20 (preparation):
Examples for etofenamate preparations:
(Amount of the components in mg per g of preparation)

| Example No. | 1 | 2 | 3 | 4 | 5 | 6 | 7 | 8 | 9 | 10 | 11 | 12 |
|---|---|---|---|---|---|---|---|---|---|---|---|---|
| Etofenamate | 25 | 50 | 50 | 50 | 50 | 100 | 50 | 50 | 25 | 25 | 25 | 25 |
| Water | 882 | 460 | 475 | 470 | 470 | 450 | — | — | — | 325 | 325 | 662 |
| Benzyl alcohol | 15 | — | — | — | — | — | — | — | — | — | — | — |
| 96% ethanol | — | 450 | 450 | 450 | 450 | 450 | — | — | — | — | — | — |
| 2N NaOH | — | — | — | — | — | — | — | — | — | 450 | 450 | 450 |
| Pectin | — | — | — | — | — | — | — | 160 | 160 | — | — | — |
| Klucel ® HF[1] | — | — | — | — | 24 | — | — | — | — | — | — | — |
| Meyprogat ® T 100[2] | 70 | — | — | — | — | — | — | — | — | — | — | — |
| Tylose ® MH 300 P[3] | — | 40 | — | — | — | — | — | — | — | — | — | — |
| Tylose ® MH 4000[3] | — | — | 25 | — | — | — | — | — | — | — | — | — |
| Tylose ® MH 1000[3] | — | — | — | 25 | — | — | — | — | — | — | — | — |

| Example No. | 1 | 2 | 3 | 5 | 5 | 6 | 7 | 8 | 9 | 10 | 11 | 12 |
|---|---|---|---|---|---|---|---|---|---|---|---|---|
| Eudispert ®[4] | — | — | — | — | 6 | — | — | — | — | — | — | — |
| Eudragit ® L 100[5] | — | — | — | — | — | — | — | — | — | 200 | — | — |
| Eudragit ® L 100-55[6] | — | — | — | — | — | — | — | — | — | — | 200 | — |
| Eudragit ® S 100[7] | — | — | — | — | — | — | — | — | — | — | — | 133 |
| Gelatine | — | — | — | — | — | — | — | 160 | 160 | — | — | — |
| Plastibase ®[8] | — | — | — | — | — | — | — | 470 | 487 | — | — | — |
| Sodium carboxy-methylcellulose | — | — | — | — | — | — | — | 160 | 160 | — | — | — |
| Menthol | 8 | — | — | — | — | — | — | — | 8 | — | — | — |

| Example No. | 13 | 14 | 15 | 16 | 17 | 18 | 19 | 20 |
|---|---|---|---|---|---|---|---|---|
| Etofenamate | 10 | 25 | 50 | 100 | 50 | 10 | 25 | 50 |
| Water | 867 | 852 | 827 | 777 | 857 | 515 | 500 | 475 |
| Benzyl alcohol | 15 | 15 | 15 | 15 | 15 | — | — | — |
| 96% ethanol | — | — | — | — | — | 450 | 450 | 450 |
| Pectin: 100 | 100 | 100 | 100 | 70 | — | — | — | |
| Klucel ® HF[9] | — | — | — | — | — | 25 | 25 | 25 |
| Menthol | 8 | 8 | 8 | 8 | 8 | — | — | — |

[1]Klucel ® HF is a hydroxypropylcellulose (Hercules Filter Corp.)
[2]Meyprogat ® T 100 is a galactomannan (Meyhall Chemical GmbH)
[3]Tylose ® mH 300 P, 4,000 and 1,000 are methylcelluloses and methylhydroxyethylcelluloses (Hoechst AG)
[4]Eudispert ® is a copolymer of methyl methacrylate and methacrylic acid (Rohm Pharma GmbH)
[5,6,7]Eudragit L 100, L 100-55, S 100 are copolymers based on methacrylic acid and methyl methacrylate (Rohm Pharma GmbH)
[8]Plastibase ® consists of polyethylene and liquid paraffin (E.R. Squibb & Sons, Inc.)
[9]Klucel ® HF is a hydroxypropylcellulose (Hercules Filter Corp.)

It is, of course, possible to combine these components. In this connection, the addition of alcohols and/or water and, where appropriate, flavorings, preservatives and colorants is possible.

Alcohols are essentially lower alcohols, preferably ethanol.

The adhesive emulsions according to the invention generally contain
1 to 10 parts by weight of etofenamate,
1 to 20 parts by weight of swelling agent,
60 to 90 parts by weight of water,
and, where appropriate, flavorings such as menthol preservatives and/or colorants.

A process for the preparation of etofenamate-containing medicaments for the treatment of inflammations in the region of the oral cavity which are caused by bacteria, viruses or fungi has also been found and is characterized in that etofenamate is mixed with the liquid components, homogenized at 30 to 70° C. and then, with stirring, the solid components are introduced.

In general, the homogenization is carried out at 30 to 70° C., preferably at about 50° C.

The solid components are essentially the above-mentioned auxiliaries. Liquid components are essentially the abovementioned alcohols and water.

EXAMPLE 21 (use)

1. Demonstration of efficacy in an animal experiment:
(a) Test substance

A 2.5% by weight ethanolic solution (base) of etofenamate was used.

(b) Test design:

Based on the method published in Caries Res. 19, 516–518 (1985) periodontitis was induced in 6 groups each of 14 Wistar rats (7 ♂, 7 ♀) by feeding a special diet (2,000 M) with the addition of 1% rat hairs. Half of the animals (3 groups) had been infected before the start of the test by oral administration of a suspension of Actinomyces viscosus Nyl organisms in order to increase the progression of the periodontitis.

The groups were divided up as follows for the test, which lasted 9 weeks:

| Group 1 | (without A. viscosus) | no therapy |
|---|---|---|
| Group 2 | (with A. viscosus) | |
| Group 3 | (without A. viscosus) | administration of |
| Group 4 | (with A. viscosus) | the base |
| Group 5 | (without A. viscosus) | treatment with |

| | | |
|---|---|---|
| -continued | | |
| Group 6 | (with A. viscosus) | etofenamate + base |

(c) Test procedure:

The test animals in groups 5 and 6 received 3 × 0.08 ml of etofenamate solution each day at intervals of 8 hours, corresponding to a daily dose of active compound of 60 mg/kg body weight based on an initial weight of 100 g. The active substance was administered directly into the oral cavity of the animals using a tuberculin syringe (without needle). The base containing no active compound was also administered in the same way and in the same frequency and amount (3×0.08 ml/day) to the animals in groups 3 and 4.

(d) Test results:

The animals were examined after the test. The loss of alveolar bone was determined by the method in Archs. Oral Biol. 27, 651–658 (1987) as a parameter for the extent of periodontal inflammation. It emerged from this that the animals treated with the active substance exhibited statistically significantly less periodontal bone destruction than the animals which were not treated or received only the base.

What is claimed is:

1. A method for the treatment of bacterial, viral or fungicidal inflamations in the region of the oral cavity comprising applying to the region of the oral cavity an adhesive emulsion composition containing an effective amount of etofenamate.

2. A method according to claim 1 wherein said composition contains 0.5 to 20% by weight of etofenamate.

3. An adhesive emulsion composition useful in the treatment of bacterial, viral or fungicial inflamations in the region of the oral cavity comprising an effective amount of etofenamate, a suitable carrier and a swellable hydrophilic natural, semi-synthetic or synthetic polymer.

4. A composition according to claim 3, comprising 0.5 to 20% by weight of etofenamate.

5. A composition according to claim 3, wherein said hydrophilic natural, semi-synthetic or synthetic polymer is gelatin, pectin, alginic acid, sodium alginate, polymannuronic acid obtained from brown algae or the alkaline metal salts thereof, gum arabic, tragacanth, galactomannan, karaya gum, a cellulose ether, polymethacrylic acid and the salts thereof, polymethylmethacrylic acid and the salts thereof or polyvinylpyrrolidone.

6. A composition according to claim 3, comprising 1 to 10 parts by weight of etofenamate, 1 to 20 parts by weight of swelling agent, 60 to 90 parts by weight of water.

7. A composition according to claim 3, comprising water and one or more alcohols.

8. A process for the preparation of an adhesive emulsion composition according to claim 3, comprising mixing etofenamate with the liquid components of the composition, homogenizing the mixture of etofenamate and liquid components at 30 to 70° C. and then introducing the solid components of the composition.

9. A process according to claim 8, wherein the liquid components comprise water and alcohols and the solid components comprising a swellable, hydrophilic, natural, semi-synthetic or synthetic polymer.

* * * * *